United States Patent
Olson et al.

(10) Patent No.: US 6,297,424 B1
(45) Date of Patent: Oct. 2, 2001

(54) ABSORBENT ARTICLES HAVING WETNESS INDICATING GRAPHICS PROVIDING AN INTERACTIVE TRAINING AID

(75) Inventors: Christopher Peter Olson; Kathleen Irene Ratliff; Shirlee Ann Weber, all of Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/333,222

(22) Filed: Jun. 15, 1999

(51) Int. Cl.$^7$ .................................................. A61F 13/15

(52) U.S. Cl. ................ 604/361; 604/385.01; 604/385.23

(58) Field of Search .................................... 604/361, 364, 604/385.01, 385.23, 386, 392, 396; 116/200, 206, 207, 208, 211; 128/886

(56) References Cited

U.S. PATENT DOCUMENTS

| | | |
|---|---|---|
| H1376 | 11/1994 | Osborn, III et al. . |
| 2,787,238 | 4/1957 | Luce . |
| 3,004,895 | 10/1961 | Schwartz . |
| 3,675,654 | 7/1972 | Baker et al. . |
| 3,702,610 | 11/1972 | Sheppard et al. . |
| 3,759,261 | 9/1973 | Wang . |
| 3,898,172 | 8/1975 | Reif et al. . |
| 3,918,454 | 11/1975 | Korodi et al. . |
| 3,952,746 | 4/1976 | Summers . |
| 4,022,211 | * 5/1977 | Timmons et al. ............ 128/287 |
| 4,192,311 | 3/1980 | Felfoldi . |
| 4,231,370 | 11/1980 | Mroz et al. . |
| 4,249,532 | 2/1981 | Polansky et al. . |
| 4,287,153 | 9/1981 | Towsend . |
| 4,292,916 | 10/1981 | Bradley et al. . |
| 4,327,731 | 5/1982 | Powell . |
| 4,507,121 | 3/1985 | Leung . |
| 4,663,220 | 5/1987 | Wisneski et al. . |
| 4,704,116 | 11/1987 | Enloe . |
| 4,705,513 | 11/1987 | Sheldon et al. . |
| 4,735,622 | 4/1988 | Acuff et al. . |
| 4,743,238 | 5/1988 | Colon et al. . |
| 4,810,562 | 3/1989 | Okawa et al. . |
| 4,812,053 | 3/1989 | Bhattacharjee . |
| 4,834,733 | 5/1989 | Huntoon et al. . |
| 4,895,567 | 1/1990 | Colon et al. . |
| 4,903,254 | 2/1990 | Haas . |
| 4,909,879 | 3/1990 | Ball . |
| 4,931,051 | 6/1990 | Castello . |
| 4,940,464 | 7/1990 | Van Gompel et al. . |

(List continued on next page.)

FOREIGN PATENT DOCUMENTS

| | | |
|---|---|---|
| 3810473 A1 | 10/1989 | (DE) . |
| 0021492 A1 | 1/1981 | (EP) . |
| 0148115 A1 | 7/1985 | (EP) . |
| 0203715 A2 | 12/1986 | (EP) . |
| 0217032 A2 | 4/1987 | (EP) . |
| 0 286 543 A2 | 10/1988 | (EP) . |
| 0776645 A1 | 6/1997 | (EP) . |
| 0813850 A2 | 12/1997 | (EP) . |

(List continued on next page.)

Primary Examiner—John G. Weiss
Assistant Examiner—Jamisue A Webb
(74) Attorney, Agent, or Firm—Thomas M. Gage (57) ABSTRACT

A disposable absorbent article such as a training pant includes wetness indicating graphics that provide an interactive training aid. The interactive graphics can include a permanent character graphic and one or more active object graphics, which "appear" or "disappear" from view in response to exposure to urine or the environment. The interactive graphics can also include a story line in which the permanent character graphic is illustrated performing an activity involving the active object graphic. The wetness indicating feature and the graphic story line allow the caregiver to interact with the child in an educational and motivational manner to enhance the toilet training process.

24 Claims, 7 Drawing Sheets

U.S. PATENT DOCUMENTS

| | | |
|---|---|---|
| 4,987,849 | 1/1991 | Sherman . |
| 5,035,691 | 7/1991 | Zimmel et al. . |
| 5,045,283 | 9/1991 | Patel . |
| 5,046,272 | 9/1991 | Vogt et al. . |
| 5,053,339 | 10/1991 | Patel . |
| 5,058,088 | 10/1991 | Haas et al. . |
| 5,066,711 | 11/1991 | Colon et al. . |
| 5,078,708 | 1/1992 | Haque . |
| 5,089,548 | 2/1992 | Zimmel et al. . |
| 5,104,116 | 4/1992 | Pohjola . |
| 5,130,290 | 7/1992 | Tanimoto . |
| 5,133,087 | 7/1992 | Machida et al. . |
| 5,167,652 | 12/1992 | Mueller . |
| 5,197,958 | 3/1993 | Howell . |
| 5,224,405 | 7/1993 | Pohjola . |
| 5,226,992 | 7/1993 | Morman . |
| 5,286,543 | 2/1994 | Ungpiyakul et al. . |
| 5,354,289 | 10/1994 | Mitchell et al. . |
| 5,364,132 | 11/1994 | Haas et al. . |
| 5,389,093 | 2/1995 | Howell . |
| 5,411,295 | 5/1995 | Bates et al. . |
| 5,435,010 | 7/1995 | May . |
| 5,458,590 | 10/1995 | Schleinz et al. . |
| 5,683,752 | 11/1997 | Popp et al. . |
| 5,766,212 | 6/1998 | Jitoe et al. . |
| 5,766,389 | 6/1998 | Brandon et al. . |
| 5,897,541 | 4/1999 | Uitenbroek et al. . |

FOREIGN PATENT DOCUMENTS

| | | |
|---|---|---|
| 2541872 A3 | 9/1984 | (FR) . |
| 2559037 A1 | 8/1995 | (FR) . |
| 2022423 A | 12/1979 | (GB) . |
| 58174601 A | 10/1983 | (JP) . |
| 1075980 A | 3/1989 | (JP) . |
| 9140742 | 6/1997 | (JP) . |
| WO 8604219 A1 | 7/1986 | (WO) . |
| WO 8700945 A1 | 2/1987 | (WO) . |
| WO 9500099 A1 | 1/1995 | (WO) . |

* cited by examiner

ABSORBENT ARTICLES HAVING WETNESS INDICATING GRAPHICS PROVIDING AN INTERACTIVE TRAINING AID

BACKGROUND OF THE INVENTION

The present invention relates to absorbent articles, and more particularly to absorbent articles having wetness indicating graphics providing an interactive training aid.

The toilet training process may incorporate a wide variety of different aspects, including many training techniques and training aids that may be used by parents and caregivers, hereinafter simply referred to as caregivers. One aspect of the total toilet training process is the change from diapers to training pants to help the child understand that he or she should now use the toilet just like adults. Another aspect of the total toilet training process includes caregiver instruction as a positive encouragement and reinforcement to the child that he or she should now be using a toilet instead of diapers. Although the use of training pants and positive encouragement from the caregiver has been helpful in the toilet training process, there is still much room for improvement. Specifically, caregivers are still searching for easier and quicker ways to guide their children successfully through the toilet training process.

Many caregivers have difficulty in determining the readiness of a child to begin the toilet training process, and underestimate the difficulty of teaching the toilet training process to young children. If a child does not respond to an initial toilet training instruction or introduction, the caregiver can at a loss for finding techniques, methods, or teaching tools to encourage the child to master the art of toilet training. Thus, while various teaching tools such as books, videotapes, charts with stickers, personalized toilets, and interactive toilet training kits are available, there remains a need for new and improved educational and motivational mechanisms to facilitate the toilet training process.

SUMMARY OF THE INVENTION

In response to the discussed deficiencies associated with prior absorbent garments, an absorbent article has been developed that provides toilet training aid benefits through the use of interactive graphics that inform the caregiver and child when an accident has occurred. The interactive graphics can include a permanent character graphic and one or more active object graphics. The object graphics are referred to as "active" because they are constructed to "disappear" or "appear" from view, particularly when the child has an accident and the active object graphic is contacted with urine, but also when the product is in use and the disappearance or appearance occurs over time as a result of exposure to the environment, such as molecules in the air. The interactive wetness indicating graphics can also include a story line in which the permanent character graphic is illustrated performing an activity involving the active object graphic. In this way, the absorbent article may permit the caregiver to interact with the child regarding the story line created by the graphics and may provide an opportunity for the caregiver to teach the child important lessons regarding toilet training due to the active nature of the object graphic.

Hence, in one embodiment, the invention concerns an absorbent article including an outer cover having an interior surface and an opposite exterior surface, and an absorbent assembly disposed on the interior surface of the outer cover. The absorbent article also includes a permanent character graphic and an active object graphic that are disposed on the outer cover, with the permanent character graphic being interactively interrelated with the active object graphic.

The term "active graphic" as used herein refers to an appearing graphic, a fading graphic, or a combination of appearing and fading graphics. The term "appearing graphic" is used herein to refer to a graphic that becomes visible or becomes significantly more visible when exposed to urine, or that becomes visible or becomes significantly more visible with the passage of time when exposed to the environment but not exposed to urine. Conversely, the term "fading graphic" is used herein to refer to a graphic that becomes invisible or significantly less visible when exposed to urine, or that becomes invisible or significantly less visible with the passage of time when exposed to the environment but not exposed to urine.

In particular embodiments, the active graphic can comprise a fading graphic which is formed from an ink that is soluble in aqueous solutions such as urine. The ink is positioned in the absorbent article so that it becomes wet and dissolves when the product is insulted with liquid. Once dissolved, the ink washes away from the outer cover and is obscured by the outer cover. As a result, the active graphic seems to disappear from view.

Suitable urine-soluble inks are available from a variety of commercial vendors, such as Sun Chemical Corp. of Philadelphia, Pa., USA under the trade designation AQUA DESTRUCT. Particular urine-soluble compositions are disclosed in U.S. Pat. No. 4,022,211 issued May 10, 1977 to Timmons et al., which is incorporated herein by reference. The ink color can be selected to provide a pleasing appearance and graphic impact, including fading rapidly upon contact with liquid. To facilitate rapid fading, the fading graphics can comprise line drawings having a line width of from about 1 to about 2 millimeters.

The active graphic can also comprise a fading or an appearing graphic which is formed from a composition such as an ink or adhesive that changes color when exposed to an aqueous solution such as urine. A color change composition can be adapted to blend in with a background or surrounding color, either before or after exposure to the aqueous solution. Suitable compositions of this color-change type are available from a variety of commercial vendors, such as a pH-change/color-change hot melt adhesive available from Findley Adhesives, Inc. of Wauwatosa, Wis., USA. Alternatively, the active graphic can comprise pH sensitive inks, fugitive inks, colored absorbent particles, hydratable salts, moisture sensitive films, enzymes, heat sensitive inks and dyes, or the like.

Fading graphics can simply disappear from view, relative to the exterior surface of the outer cover. For example, fading object graphics can be made to disappear into a permanent background graphic. Representative examples include an object graphic such as yellow fish disappearing or fading into a background graphic such as blue water or green weeds; an object graphic such as pink flowers fading into a background graphic such as a green lawn; an object graphic such as lavender sand toys fading into a background graphic such as tan sand; an object graphic such as pink sea shells fading into a background graphic such as tan sand; an object graphic such as small animals fading into a background graphic such as a jungle scene; an object graphic such as frogs fading into a background graphic such as water lilies; an object graphic such as green toys fading into a background graphic such as a yellow floor or blanket area; an object graphic such as pink angels fading into a background graphic such as blue clouds; an object graphic such as a red bone fading from a background graphic such as the inside of a dog's dish; an object graphic such as a cat's yellow yarn balls fading from a background graphic such as a green checkered floor; an object graphic such as a toy car disappearing from a background graphic such as a road; or the like.

The active graphic can also be configured to appear over time due to exposure to the environment. In particular, the active graphic can be responsive to time intervals, temperature levels, oxygen levels, or the like, and combinations thereof. Various visual indicators that appear over time in response to particular conditions are disclosed in U.S. Pat. No. 5,058,088 issued Oct. 15, 1991 to Haas et al.; U.S. Pat. No. 5,053,339 issued Oct. 1, 1991 to Patel; U.S. Pat. No. 5,045,283 issued Sep. 3, 1991 to Patel; U.S. Pat. No. 4,987,849 issued Jan. 29, 1991 to Sherman; U.S. Pat. No. 4,903,254 issued Feb. 20, 1990 to Haas; U.S. Pat. No. 4,812,053 issued Mar. 14, 1989 to Bhattacharjee; and U.S. Pat. No. 4,292,916 issued Oct. 6, 1981 to Bradley et al.; all of which are incorporated herein by reference. An active graphic that appears over time may be applied to the product when use is initiated, or formed as an integral component of the product.

In contrast to active graphics, the term "permanent graphic" is used herein to refer to a graphic that does not substantially change its degree of visibility when the absorbent article is insulted with urine and when the absorbent article is exposed to the environment, in simulated use conditions. The change in visibility of a graphic or a portion of a graphic can be determined based on a person's observation of the graphic before and after the article containing the graphic is exposed to liquid. For purposes hereof, an article is exposed to liquid by immersing the article completely in an aqueous solution containing 0.9 weight percent sodium chloride, used at room temperature ($\cong 23°$ C.), for a period of twenty minutes. After 20 minutes the product is removed from the aqueous solution and placed on a TEFLON™ coated fiberglass screen having 0.25 inch openings, which is commercially available from Taconic Plastics Inc., Petersberg, N.Y., USA, which in turn is placed on a vacuum box and covered with a flexible rubber dam material. A vacuum of 3.5 kilopascals (0.5 pounds per square inch) is drawn in the vacuum box for a period of 5 minutes, after which the article is removed and observed. The person with normal or corrected vision of 20–20 should make the observations from a distance of 1 meter in an environment providing 30 footcandles (320 Lux) of illumination. Changes in the visibility of the graphic should be identified, and distinguished where necessary from changes in the color of other materials such as fluff pulp within an absorbent assembly. Desirably, the permanent graphic can be configured so that the entire graphic also does not substantially change its appearance, size or shape when the product is insulted with liquid or exposed to the environment.

The graphics of the absorbent article can be constructed to provide a story line involving a permanent character graphic and an active object graphic. The term "character graphic" is used herein to refer to a graphic containing an anthropomorphous image, and in particular an image having or suggesting human form or appearance which ascribes human motivations, characteristics or behavior to inanimate objects, animals, natural phenomena, cartoon characters, or the like. Ideally the character graphic would be suitable for children's underwear and could be utilized to motivate children to wear the pants and use a potty or toilet. To that end, the character graphics can be associated with popular characters in the media, advertising or well known in a particular culture. Ideally they are characters that the child or caregiver care about and want to identify with. Ideally the child can imagine himself or herself taking the place of the character. The character graphics can comprise permanent graphics, active graphics, or both permanent and active graphics.

The role of the character graphic can be to help a child feel like a BIG KID® (a registered trademark of Kimberly-Clark Corporation) and to motivate them to become toilet trained. The character graphic can also give parents and caregivers an interactive element for use during toilet training. One embodiment comprises a permanent character graphic that cannot complete some action or observation after the fading graphics have disappeared. This facilitates nonthreatening and gentle communications between the child and caregiver when the child has had an accident and wet his or her pants. The character graphic is a third party that the caregiver can use to deflect blame and shame from the child while still communicating the desire that the child not wet his or her pants. It may be easier for the child to accept criticism when the caregiver seems to be talking about a third person. It may also be less stressful for the caregiver because he or she does not need to directly confront the child over the mistake. Similarly, the character graphic may provide a source of comfort for the child and a buddy who reduces stress during the training period.

The character graphic can desirably comprise a portion of the entire training pant graphic that sets up a theme for the illustrated scene. As such, the character graphic can provide an opportunity for educational interaction between the child and the parent or caregiver. More specifically, the parent or caregiver can use the graphic story-line to make up a game or story for the purpose of toilet training progress. In the case of fading object graphics which "disappear" when the child wets his or her training pant, the caregiver may take an approach such as: "See the little bear in the boat fishing. Try not to go potty in your training pants, because if you do the fish under the boat will disappear."

Suitable character graphics can include animals, people, inanimate objects, natural phenomena, cartoon characters, or the like that can or can not be provided with human features such as arms, legs, facial features or the like. For purposes of enhanced toilet training, it may be desirable for the character graphic to be familiar to the child, such as an identifiable cartoon character. The character graphics should at least be a type that the child can relate to, examples of which could include animals, toys, licensed characters, or the like. Character graphics can be made more personable and friendly to the child by including human-like features, human-like expressions, apparel, abilities, or the like. By way of illustration, an animal character graphic can be shown smiling, wearing clothing, playing sports, fishing, driving, playing with toys, or the like. In particular embodiments, the character graphic can desirably be created to project an appearance that could be described as friendly, positive, non-intimidating, silly, independent, inspirational, active, expressive, dauntless and/or persevering.

As referenced above, the permanent character graphic is desirably interactively interrelated with the active object graphic. The term "object graphic" is used herein to refer to a graphic representing an object or thing, which can include an inanimate object or a character.

As used herein, the term "interactively interrelated" is used to mean that the character graphic is illustrated to be involved in or performing an action or activity, and the object graphic is the object of or is associated with the action or activity. Without wishing to be limited to the specific embodiments listed, suitable examples of a character graphic interactively interrelated with an object graphic can include: the character graphic holding or using a racquet, bat, glove, other sporting equipment or the like and the object graphics comprising balls, related sporting equipment or the like; the character graphic illustrated on a soccer field, football field, basketball court or the like environment and the object graphics comprising balls, related equipment or toys; the character graphic holding a butterfly net or the like and the object graphics comprising butterflies or the like; the character graphic holding a fishing pole, sitting in a boat or the like and the object graphics comprising fish, inflatable water toys or the like; the character graphic holding flowers, plants, gardening tools or the like and the object graphics comprising flowers or plants; the character graphic feeding, training or nurturing the object graphics which comprise animals, plants or the like; the character graphic playing in a specific environment such as a doll house, barn yard or the like and the object graphics comprising dolls, animals or the like which are specifically adapted to the environment; the character graphic holding or using a telescope or the like and the object graphics comprising stars, planets or the like; the character graphic comprising a racecar and the object graphic comprising race flags; the character graphic comprising a submarine and the object graphic comprising fish, bubbles, shells or the like; the character graphic comprising a pet or other animal and the object graphics comprising dog bones, pet toys, food or the like; the character graphic comprising a large a sandbox and the object graphic comprising toys in the sandbox; the character graphic comprising a dog near a large dog dish and the object graphic comprising the dog bones inside or near the dog dish; or other suitable interactively interrelated graphics.

The absorbent article can also include a permanent object graphic that facilitates the interactive nature of the graphics, and provides the caregiver with greater opportunity to develop a story for interacting with the child. Hence, in one embodiment, an absorbent article includes an outer cover having in interior surface and an opposite exterior surface, and an absorbent assembly disposed on the interior surface of the outer cover. A permanent character graphic, a permanent object graphic, and an active object graphic are each disposed on the outer cover. The permanent character graphic is interactively interrelated with the active object graphic, and the permanent object graphic is related in subject matter to the active object graphic.

As used herein, the phrase "related in subject matter" refers to the situation where the subject matter of one graphic is the same as or is linked to the subject matter of another graphic. The subject matter relationship can be between two or more text messages, between two or more pictorial images, or between a combination of one or more text messages and one or more pictorial images. The term "text message" means a graphic consisting of one or more alphanumeric symbols, and the term "pictorial image" means a graphic consisting of one or more pictures. The terms "text image" and "pictorial image" are mutually exclusive as used herein. The general term "graphic" is used herein to mean any design, pattern, or the like that is or becomes visible on an absorbent article, and specifically includes text messages that consist of one or more alphanumeric symbols, pictorial images that consist of one or more pictures, and combinations thereof.

By way of example, two pictorial images are considered related in subject matter where the images are identical; separately illustrate different sizes, shapes, colors of a common object; each illustrate one and the other of two objects that are commonly associated with one another, such as the moon and stars, a body of water and water toys, a sandbox and suitable toys, a baseball bat and ball, a barn and animals, or the like; illustrate different items used in a particular activity, such as a sporting activity, a gardening activity or the like; jointly illustrate geometrically mating or engaging elements such as a triangle and a triangularly-shaped aperture, or two halves of a zipper; each illustrate one part of a multipart picture; or the like. Similarly, two text messages are considered related in subject matter where the messages: are identical; jointly form a sentence, thought, or action such as "jump" and "up"; each refer to one and the other of two items that are commonly associated with one another, such as "bat" and "ball," "Big" and "Kid," "Big" and "Girl," or "Big" and "Boy"; jointly present a question and answer; or the like. Likewise, a text message and a pictorial image are considered to be related in subject matter where the text names, defines or describes the image; or the like.

The permanent object graphic can be interactively related to the permanent character graphic. Hence, in particular embodiments, an absorbent article includes an outer cover having an interior surface and an opposite exterior surface, and an absorbent assembly disposed on the interior surface of the outer cover. A permanent character graphic, a permanent object graphic, and an active object graphic are each disposed on the outer cover. The permanent character graphic is interactively interrelated with both the permanent object graphic and the active object graphic.

More particularly, the graphics of the absorbent article can include a permanent character graphic, one or more permanent object graphics, and one or more active object graphics, all of which are related by a common story line, which would be generally known through books, movies, or other media sources. Further, the permanent character graphic is involved in an activity utilizing the permanent object graphics, and the active object graphics are the subject of the activity. For example, the graphics can include a permanent character graphic consisting of an animal having human clothing, features and abilities engaged in an activity such as fishing using a fishing pole, which is typically an activity undertaken by humans. The permanent object graphics can comprise objects such as a boat, a lake and a fishing pole which are associated with and/or define the activity of fishing. The active object graphics can comprise a plurality of fish, which are the subject of the activity and are adapted to fade or disappear from view when the absorbent article is insulted with urine.

The permanent object graphic can alternatively be interactively unrelated to the permanent character graphic. For example, the permanent object graphic can comprise background graphics that are unrelated to the activity of the character graphic. By way of illustration, the permanent object graphics can comprise images of the sky, the sun, grass, or the like.

In use, the active graphic can appear or fade when an accident occurs and urine comes into contact with the active graphic. Desirably, the active graphic appears or fades in about 3 minutes or less, particularly in about 1 minute or less, and more desirably in about 20 seconds or less, when the absorbent article is insulted with 200 milliliters or more of urine, and more desirably about 40 to about 60 milliliters or more of urine.

The changed condition of the graphic presents a tool for the caregiver to interact with the child and explain why the graphic changed. This is particularly useful at the stage of toilet training where the child is being taught to be aware of going potty and the need to use the bathroom. The combination of story line graphics and active graphics are believed to make children more interested in the toilet training process and therefore lead to enhanced results.

When the active graphic is a fading graphic, the training opportunity is based on the fact that the activity being performed by the permanent character graphic is halted when the child has an accident and the object graphics disappear. A slight sense of disappointment may be gently communicated to the child, because the object graphics are no longer present and the character graphic can no longer interact with the object graphics. A caregiver might take a positive approach: "Try not to wet in your pants so the Bear at the beach still has his sand toys to play with." Significantly, this can be used as a motivational basis for teaching the child that it is within the child's control to permit the activity to continue for as long as the child can go without wetting his or her pants.

Another training opportunity exists when fading graphics are employed in the present absorbent articles, such as training pants. The caregiver can teach the child that the child is supposed to interrupt playing when the child has to use the bathroom, similar to the character graphic having to cease its activity when the active object graphics disappear.

When the active graphic is an appearing graphic as opposed to a fading graphic, the training opportunity is based on the fact that the caregiver can explain the appearance of a new graphic for a reward, therefore a more positive approach can be taken. For example, the active graphic can be adapted to appear over time, and it may be viewed as a reward for the child for staying dry. It can in this case be used as a tool to identify toilet training queues. For instance, if an active graphic appeared over time, such as one every hour while staying dry, the caregiver could say "Hey, look how good you are doing; you stayed dry for 2 hours."

The active graphic can alternatively change color to a brighter and/or darker color. By way of illustration, a teddy bear outlined and colored very pale, such as yellow or tan, can when in contact with urine turn into bright reds, greens, and/or blues. Alternatively, only the outline of the active graphic can be present and a pattern or solid color can appear over time or when in contact with urine. For example, the active graphic can include an outline of a fire truck, which fills in to become a solid color when urine comes in contact with the truck.

To provide proper focus on the permanent character graphic, the permanent character graphic can be positioned in the front waist region along or near the longitudinal centerline of the product. The permanent character graphic, or a supplemental or complementary permanent character graphic, can be positioned in the back waist region along or near the longitudinal centerline of the product. In particular embodiments, a front view of the character graphic is shown in the front waist region and a back view of the same character graphic is shown in the back waist region. The permanent character graphic can be spaced from the first and second end edges of the product, for example, approximately 5 centimeters from the front end edge.

The active object graphics can be positioned closer to the transverse centerline of the product than the permanent character graphic. In particular embodiments, the active object graphics are positioned between the transverse centerline of the product and the permanent character graphic so as to be properly focused and not hidden from view during use. Locating the active graphics in the crotch region of the product, near the target spot for urination, can also assist with rapid exposure of the active graphic to urine upon insult. For active graphics that are triggered by contact with urine, it is desirable for the active graphics to be located on the area of the outer cover that is most likely to experience wetness during the first void. Of course, alternative positioning of the permanent and active characters are possible, such as the permanent character graphic in the crotch region and the active object graphic in one of the waist regions, both permanent and active graphics in one or both of the waist regions or the crotch region, or the like. The active object graphics can but need not necessarily be positioned on one or more sides of the permanent character graphic, such as "floating" under the character graphic. Alternatively, the permanent character graphic can surround the active object graphic.

In one particular embodiment, all of the active object graphics are located in a distinct active graphic region where the child can focus attention. The active graphic region suitably has a length dimension measured parallel to the longitudinal centerline of about 10 centimeters, more particularly about 9 centimeters, and a width dimension measured parallel to the transverse centerline of about 6 centimeters. The active graphic region may, for instance, be spaced from the first end edge of the product by approximately 13 to 16 centimeters.

There can be one or more active object graphics. It is believed desirable to use a plurality of active object graphics in order provide the greatest impact to the child. In particular embodiments, a training pant comprises 3 or more active object graphics, particularly from 4 to 8, such as 5 arranged in a 2-1-2 pattern.

The size of the active object graphics may depend in part on their number and type. It is generally preferred that the active object graphics have a size of at least about 1.5 by 1.5 centimeter and less than about 3 by 3 centimeters, and particularly at least about 1.8 by 1.8 centimeter and less than about 2.5 by 2.5 centimeters.

The overall size of the permanent character graphic can be significantly larger than the overall size of each discrete active object graphic. In particular embodiments, for instance, the permanent character graphic has a size measured by overall surface area that is at least twice as large, and more particularly at least three times as large, as the size of a single object graphic. The maximum length dimension of the permanent character graphic, measured parallel to the longitudinal centerline, is desirably about 8 to about 9 centimeters.

The permanent character graphics, the permanent object graphics and the active object graphics are suitably disposed on the outer cover. The term "disposed on" and variations thereof are intended to mean that one element can be integral with another element, or that one element can be a separate structure bonded to or placed with or placed near another element. Thus, the graphics can be formed or applied directly or indirectly to a surface of the outer cover, formed or applied between layers of a multiple layer outer cover, formed or applied to a substrate that is placed with or near the outer cover, formed or applied within a layer of the outer cover or another substrate, or other variations or combinations thereof. In particular embodiments, the graphics can be printed, sprayed, or otherwise applied directly on a layer of the outer cover. In other embodiments, the graphics can be applied to a layer placed with or near the outer cover, such as a substrate associated with the absorbent assembly, including but not limited to tissue layers, liquid handling layers, absorbent layers, or the like.

The permanent graphics can be located on the exterior surface of the outer cover to enhance the visual impact of the permanent graphics. Alternatively, however, the permanent graphics can be located on the interior surface of the outer cover or between layers of a multilayer outer cover, provided the permanent graphics remain visible from the exterior of the product.

The active graphics can be located on the interior surface of the outer cover, which is particularly desirable for active graphics that are triggered by urine in order to enhance the speed at which the graphics are contacted with urine and thus change their visual appearance. The outer cover desirably comprises a material that is formed or treated to be liquid impermeable. In alternative embodiments, the outer cover can comprise a material that is formed or treated to be at least partially liquid permeable. In this latter case, the active graphics can be located between layers of a multilayer outer cover, or, particularly for appearing graphics, on the exterior surface of the outer cover. Regardless of location, fading graphics should be visible from the exterior of the product before activation and appearing graphics should be visible from the exterior of the product after activation.

"Liquid impermeable", when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, can spread or be transported parallel to the plane of the liquid impermeable layer or laminate, but this is not considered to be within the meaning of "liquid impermeable" when used herein.

The outer cover can comprise a translucent material that has sufficient opacity, or a transparent or translucent material that is otherwise treated, to mask a urine soluble ink after it has dissolved. Such an outer cover should not be so opaque that the graphics printed on the interior surface of the outer cover or adjacent to the interior surface are obscured. Polymer films used to form the outer cover can be treated with titanium dioxide to make the film appear white and to develop sufficient opacity to mask urine, BM and dissolved inks. Examples of suitable outer cover materials include films formed of polyethylene, polypropylene, cataloy, bi-component, any polymer based extruded film, or the like. One such film is a polyethylene film having a thickness of about 0.2 millimeter (0.75 mil).

The permanent and active graphics can be formed on or applied to the outer cover or another substrate bonded to or placed with or placed near the outer cover by any suitable technique. The graphics are desirably registered with other components of the absorbent article during manufacture such that the graphics are positioned in the desired regions of the product.

For active graphics that are triggered by contact with urine, the active graphic can be in liquid communication with the absorbent assembly of the product. As used herein, the term "liquid communication" means that liquid such as urine is able to travel from one layer or element to another layer or element. The absorbent assembly can but need not include a slot or densified region, incorporate a liquid distribution layer, or the like, to channel or direct liquid to the location near the outer cover where the active graphics are located.

As noted previously, liquid soluble inks can be used to form the active graphics. It is theorized that migration of the dissolved inks away from the outer cover and into the absorbent assembly can improve the fading or disappearing quality of the active graphics. To enhance this effect, the outer cover can be attached to the absorbent assembly in a windowpane design, whereby the active graphic region of the outer cover is not bonded to the absorbent assembly and the regions of the outer cover surrounding the active graphic region are bonded to the absorbent assembly. One suitable method and apparatus for adhesively bonding the outer cover to the absorbent assembly in a windowpane design is disclosed in U.S. Pat. No. 5,683,752 issued Nov. 4, 1997 to Popp et al., which is incorporated herein by reference.

Absorbent articles suitable for use with the present invention include diapers, training pants, incontinence products, diaper pants, disposable underwear, or the like. Suitable training pants and diaper pants can have seamed side portions or refastenable side portions. The present invention is particularly suited for use with training pants or diaper pants to aid in toilet training. One particular training pant suitable for use with the present invention is disclosed in U.S. Pat. No. 4,940,464 issued Jul. 10,1990 to Van Gompel et al., which is incorporated herein by reference. The Van Gompel et al. patent describes various materials of which the training pant can be made, and a method of constructing a training pant. The training pant can also be constructed using the methods and apparatus disclosed in U.S. Pat. No. 5,766,389 issued Jun. 16, 1998 to Brandon et al., which is also incorporated herein by reference.

The above-mentioned and other features and advantages of the present invention and the manner of attaining them will become more apparent, and the invention itself will be better understood by reference to the drawings and the following description of the drawings.

DETAILED DESCRIPTION OF THE DRAWINGS

The principles of the present invention can be incorporated into a variety of absorbent articles, and particularly disposable absorbent articles. The term "disposable" refers to articles which are designed to be discarded after a limited use rather than being laundered or otherwise restored for reuse. For ease of explanation, the description hereafter will be in terms of a child's training pant.

Figure 1:
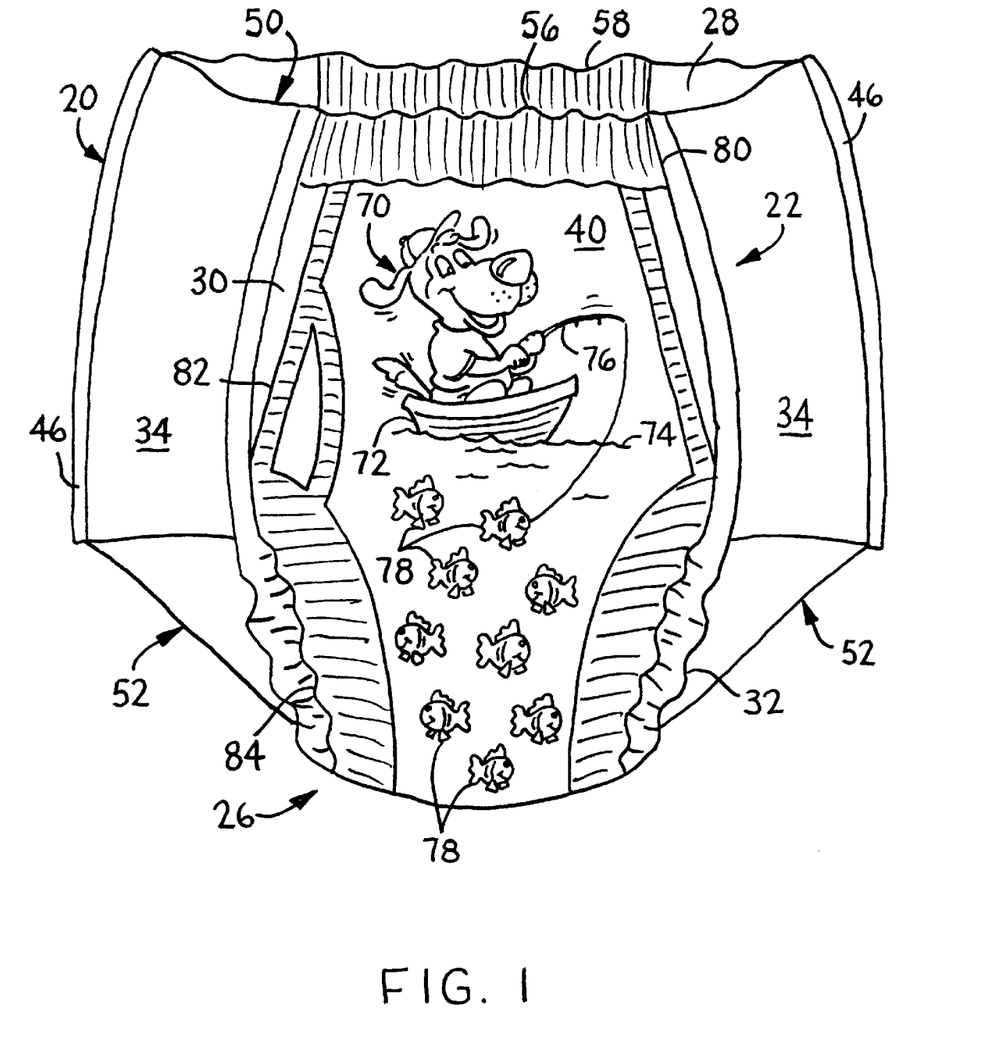
FIG. 1 illustrates a front perspective view of a training pant incorporating the principles of the present invention, showing both permanent graphics and active graphics.
Figure 2:
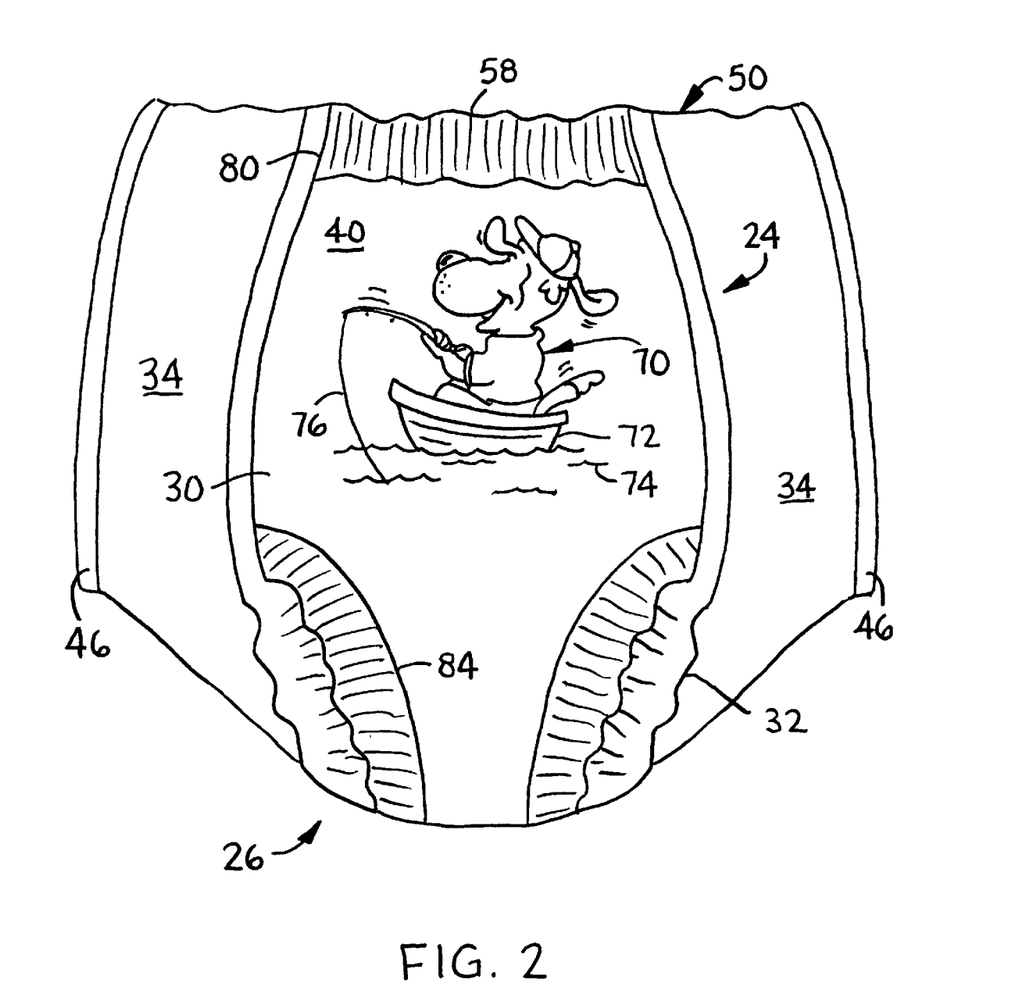
FIG. 2 illustrates a rear perspective view of the training pant of FIG. 1.
Figure 3:
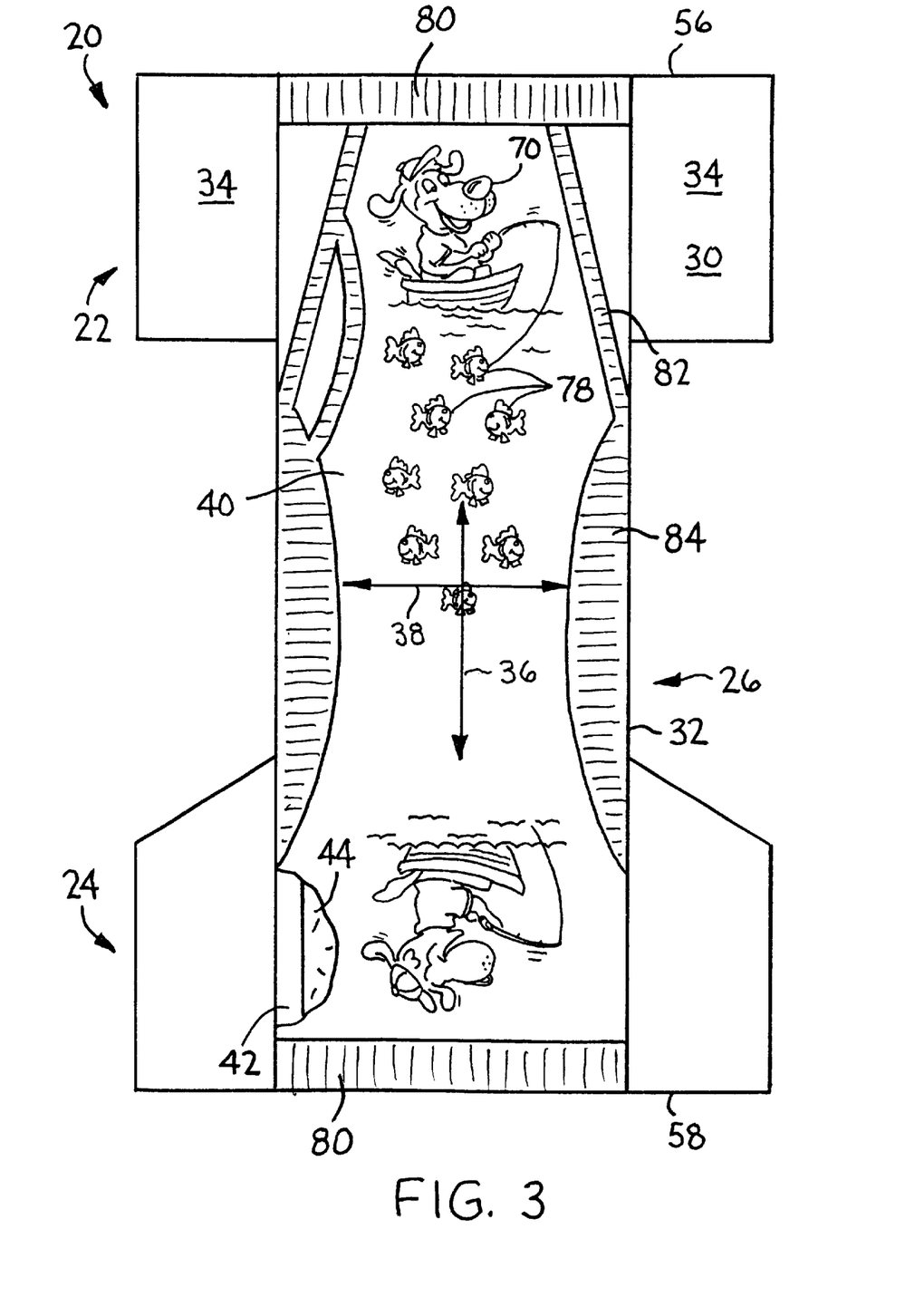
FIG. 3 illustrates a top plan, partially disassembled view of the training pant of FIGS. 1 and 2, in a stretched and laid flat condition and with portions broken away for purposes of illustration.

A training pant 20 is illustrated in a fully assembled condition in FIGS. 1 and 2 and in a partially disassembled, stretched and laid flat condition in FIG. 3. The training pant 20 defines a first or front waist region 22, a second or back waist region 24, a crotch region 26 positioned between and interconnecting the front and back waist regions, an inner surface 28 (FIG. 1) which is configured to contact the wearer, and an outer surface 30 opposite the inner surface which is configured to contact the wearer's clothing. The illustrated training pant 20 comprises an absorbent chassis 32 and a plurality of transversely opposed side panels 34. The absorbent chassis 32 and side panels 34 can be integrally formed or comprise two or more separate elements, as shown.

The training pant 20 defines a longitudinal centerline 36 (FIG. 3), a transverse centerline 38 (FIG. 3), a first or front longitudinal end edge 56, and a second or back longitudinal end edge 58. The first waist region 22 abuts the first longitudinal end edge 56, and the second waist region 24 abuts the second longitudinal end edge 58. "Longitudinal" and "transverse" have their customary meaning. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

The illustrated absorbent chassis 32 comprises an outer cover 40 and a bodyside liner 42 (FIG. 3) which is connected to the outer cover in a superposed relation. The absorbent chassis 32 also comprises an absorbent assembly 44 (FIG. 3) which is located between the outer cover and the bodyside liner, and can optionally include a pair of containment flaps (not shown).

With the training pant 20 in a fully assembled condition as illustrated in FIGS. 1 and 2, the front and back waist regions 22 and 24 are joined together by side seams 46 to define a waist opening 50 and a pair of leg openings 52. The front waist region 22 comprises the portion of the training pant 20 which, when worn, is positioned on the front of the wearer while the back waist region 24 comprises the portion of the training pant which, when worn, is positioned on the back of the wearer. The crotch region 26 of the training pant 20 comprises the portion of the training pant which, when worn, is positioned between the legs of the wearer and covers the lower torso of the wearer. The side panels 34 comprise the portions of the training pant 20 which, when worn, are positioned on the side hip regions of the wearer. The longitudinal end edges 56 and 58 of the training pant 20 are configured to encircle the waist of the wearer when worn and provide the waist opening 50.

The absorbent chassis 32 is configured to contain and/or absorb any body exudates discharged from the wearer. For example, the absorbent chassis 32 desirably although not necessarily comprises the pair of containment flaps (not shown) which can be configured to provide a barrier to the transverse flow of body exudates. Suitable constructions and arrangements for the containment flaps are generally well known to those skilled in the art and are described in U.S. Pat. No. 4,704,116 issued Nov. 3, 1987 to Enloe, which is incorporated herein by reference.

To further enhance containment and/or absorption of body exudates, the training pant 20 can include a front waist elastic member, a rear waist elastic member, and leg elastic members (not shown), as are known to those skilled in the art. Waist elastic members and leg elastic members can be operatively joined to the outer cover 40 and/or bodyside liner 42 of the training pant 20. Elastic members for the containment flaps, waist elastics and leg elastics can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic constrictive forces are imparted to the substrate. In one particular embodiment, for example, the leg elastic members comprise a plurality of dry-spun coalesced multifilament spandex elastomeric threads sold under the trade name LYCRA® and available from E. I. Du Pont de Nemours and Company, Wilmington, Del.

The outer cover 40 has an exterior surface corresponding to the outer surface 30 of the training pant and an opposite interior surface. The outer cover 40 desirably comprises a material that is substantially liquid impermeable. The outer cover 40 can be a single layer of liquid impermeable material, but desirably comprises a multi-layered laminate structure in which at least one of the layers is liquid impermeable. For instance, the outer cover 40 can include a liquid permeable outer layer and a liquid impermeable inner layer that are suitably joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wis., or from National Starch and Chemical Company, Bridgewater, N.J. The liquid permeable outer layer can be any suitable material and desirably one that provides a generally cloth-like texture. One example of such a material is a 20 gsm (grams per square meter) spunbond polypropylene nonwoven web. The outer layer can also be made of those materials of which liquid permeable bodyside liner 42 is made. While it is not a necessity for outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer is desirably manufactured from a thin plastic film, although other flexible liquid impermeable materials can also be used. The inner layer, or the liquid impermeable outer cover 40 when a single layer, prevents waste material from wetting articles, such as bedsheets and clothing, as well as the wearer and caregiver. A suitable liquid impermeable film for use as liquid impermeable inner layer, or a single layer liquid impermeable outer cover 40, is a 0.025 millimeter (1.0 mil) polyethylene film commercially available from Edison Plastics Company of South Plainfield, N.J. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

As shown in FIGS. 1–3, the training pant 20 and in particular the outer cover 40 desirably comprises one or more appearance-related components. Examples of appearance-related components include, but are not limited to, graphics; highlighting or emphasizing leg and waist openings in order to make product shaping more evident or visible to the user; highlighting or emphasizing areas of the product to simulate functional components such as elastic leg bands, elastic waistbands, simulated "fly openings" for boys, ruffles for girls; highlighting areas of the product to change the appearance of the size of the product; registering wetness indicators, temperature indicators, and the like in the product; registering a back label, or a front label, in the product; and registering written instructions at a desired location in the product.

The illustrated training pant 20, which is designed for use by young boys, includes registered outer cover graphics, including interactive wetness indicating graphics. More specifically, the training pant includes a permanent character graphic 70 in the form of a dog having human-like expressions and wearing a shirt and a hat, permanent object graphics 72, 74 and 76 in the form of a boat, curved line segments denoting the surface of water, and a fishing pole, respectively, and a plurality of active object graphics 78 representing fish. The outer cover graphics also include a simulated elastic waistband 80, a simulated fly opening 82, and simulated elastic leg bands 84, all of which can be permanent graphics.

The active object graphics 78 can be disposed on the interior surface of the outer cover 40 and are visible from the exterior surface of the outer cover. The active object graphics 78 are in liquid communication with the absorbent assembly 44, meaning that liquid such as urine is capable of moving between the active object graphic and the absorbent assembly under ordinary use conditions.

Figure 4:
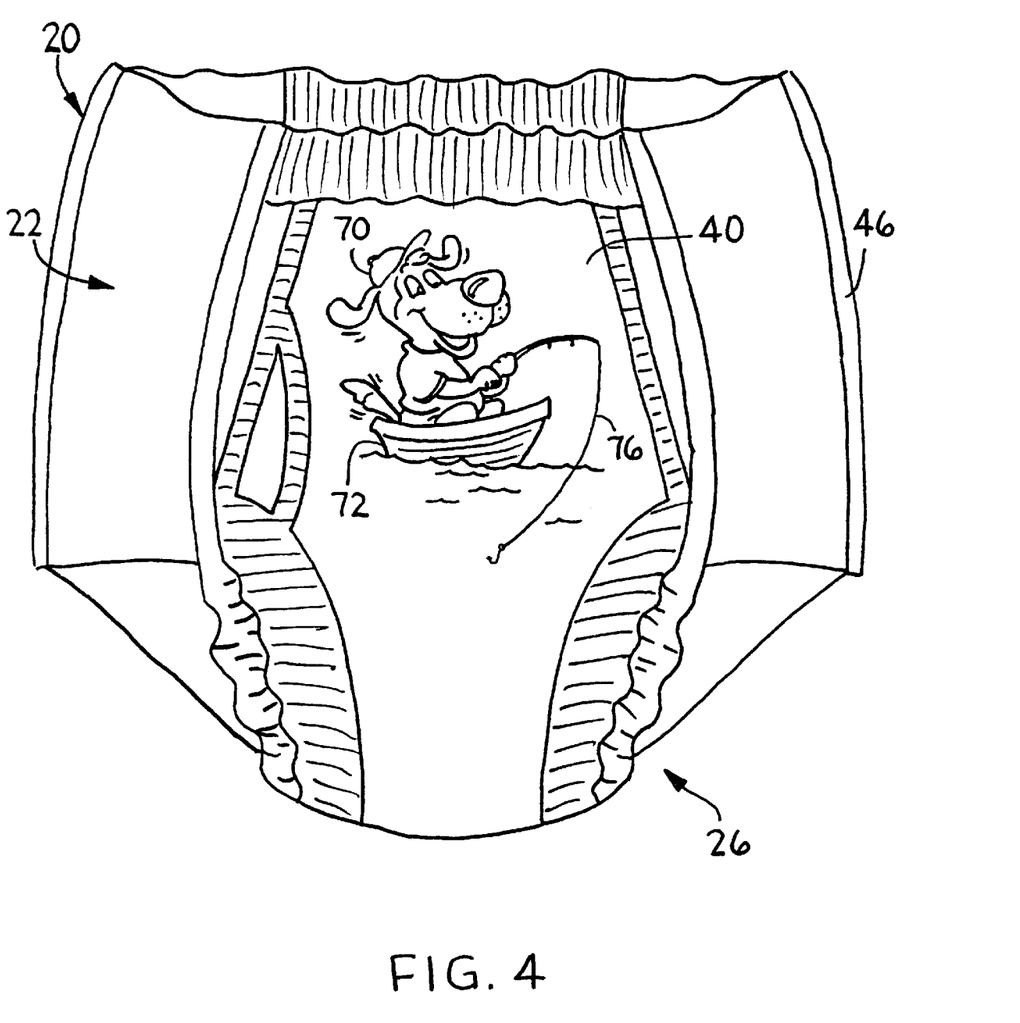
FIG. 4 illustrates a front perspective view similar to FIG. 1, although showing only the permanent graphics.

When the child wets the training pant 20, liquid is communicated to the active object graphics 78, whereupon the object graphics either dissolve, change color, appear, or the like. The effect is illustrated in FIG. 4, showing the situation where the active object graphics 78 disappear upon contact with urine. The front view of FIG. 4 shows that the active object graphics 78 are no longer present. Where appearing graphics are employed, the situation would work in reverse and the appearance of the pant would change from FIG. 4 to FIG. 1 upon liquid insult. Alternatively, the active object graphics 78 can comprise appearing graphics that are triggered upon use by exposure to the environment.

Figure 5:
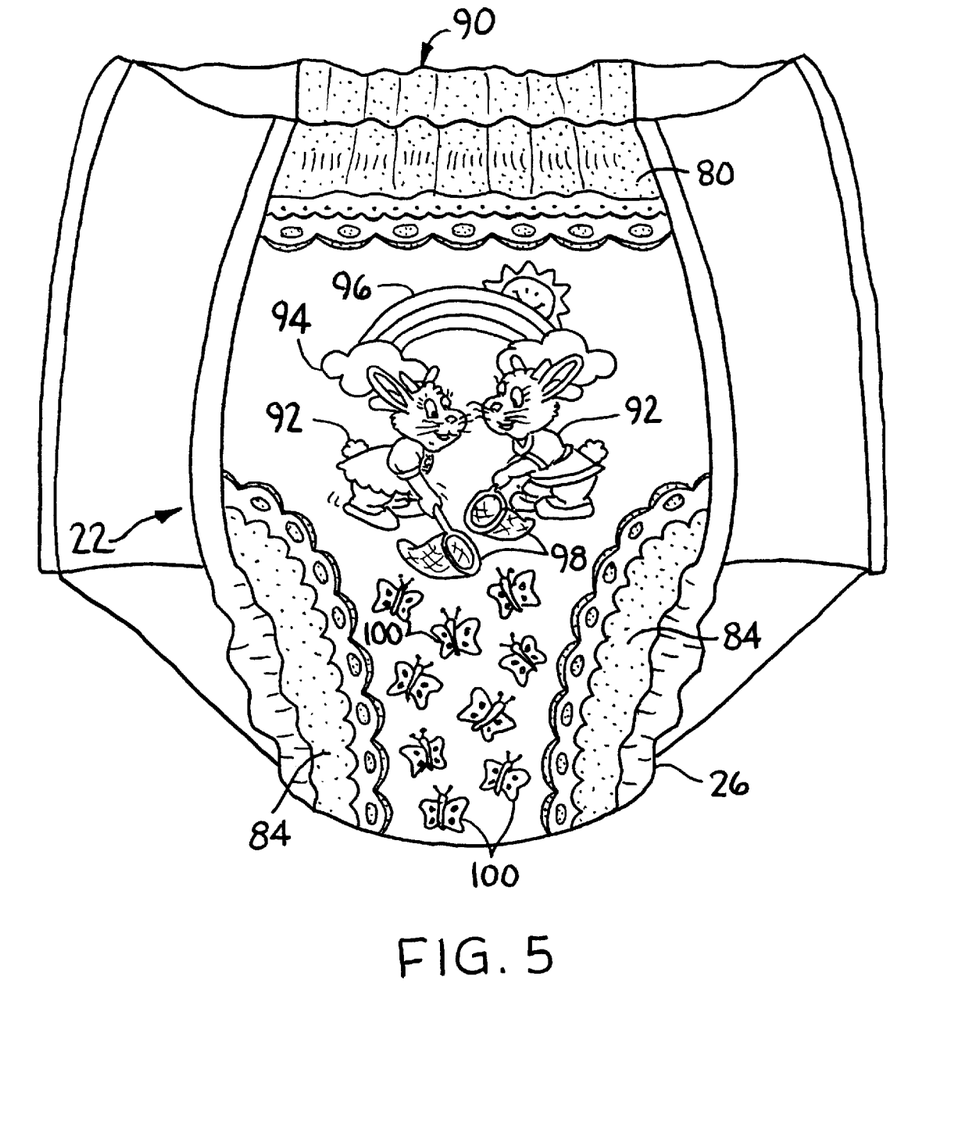
FIG. 5 illustrates a front perspective view of an alternative embodiment of a training pant incorporating the principles of the present invention.
Figure 6:
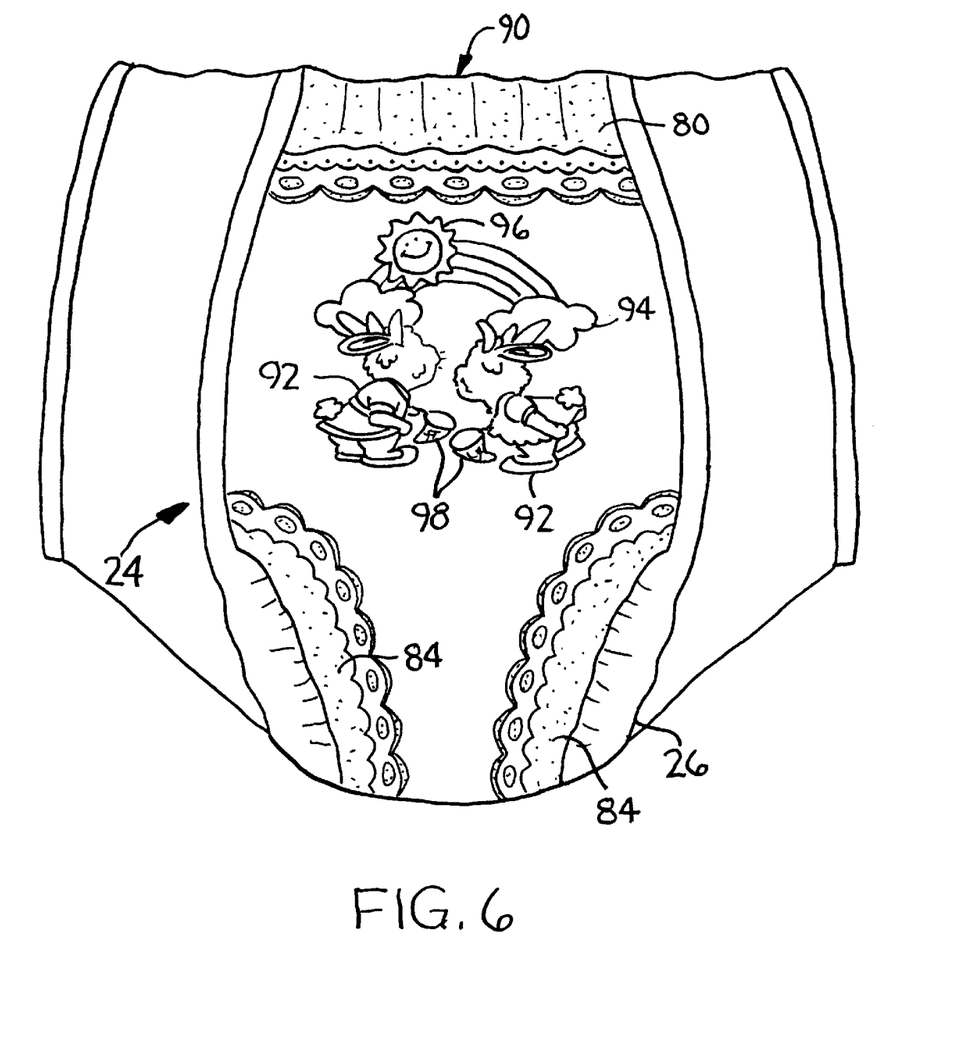
FIG. 6 illustrates a rear perspective view of the training pant of FIG. 5.

An alternative embodiment of a training pant 90 designed for use by young girls is illustrated in FIGS. 5 and 6. The illustrated training pant 90 includes permanent character graphics 92, permanent object graphics 94, 96 and 98 in the form of clouds, rainbow and sun, and butterfly nets, respectively, and a plurality of active object graphics 100 representing butterflies. The outer cover graphics also include a simulated elastic waistband 80 with ruffles, and simulated elastic leg bands 84 with ruffles, which are both permanent graphics.

The liquid permeable bodyside liner 42 generally overlies the outer cover 40 and absorbent assembly 44, and can but need not have the same dimensions as the outer cover 40. The bodyside liner 42 is desirably compliant, soft feeling, and non-irritating to the child's skin. Further, the bodyside liner 42 can be less hydrophilic than the absorbent assembly 44, to present a relatively dry surface to the wearer and permit liquid to readily penetrate through its thickness.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material may, optionally, be treated with a surfactant or otherwise processed to impart a desired level of wettability and hydrophilicity. For example, the material can be surface treated with about 0.28 weight percent of a surfactant commercially available from the Rohm and Haas Co. under the trade designation Triton X-102. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal centerline.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like.

The absorbent assembly 44 (FIG. 3) is positioned between the outer cover 40 and the bodyside liner 42, which components can be joined together by any suitable means such as adhesives as is well known in the art. The absorbent assembly 44 can be any structure which is generally compressible, conformable, non-irritating to the child's skin, and capable of absorbing and retaining liquids and certain body wastes. The absorbent assembly 44 can be manufactured in a wide variety of sizes and shapes, and from a wide variety of liquid absorbent materials commonly used in the art. For example, the absorbent assembly 44 can suitably comprise a matrix of hydrophilic fibers, such as a web of cellulosic fluff, mixed with particles of a high-absorbency material commonly known as superabsorbent material. In a particular embodiment, the absorbent assembly 44 comprises a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can comprise a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich. and Hoechst-Celanese Corporation located in Portsmouth, Va. Typically, a superabsorbent material is capable of absorbing at least about 15 times its weight in water, and desirably is capable of absorbing more than about 25 times its weight in water.

In one embodiment, the absorbent assembly 44 is generally rectangular in shape, and comprises a blend of wood pulp fluff and superabsorbent material. One preferred type of fluff is identified with the trade designation CR1654, available from Kimberly-Clark Corporation, Neenah, Wis., and is a bleached, highly absorbent sulfate wood pulp containing primarily soft wood fibers. As a general rule, the superabsorbent material is present in the absorbent assembly 44 in an amount of from about 5 to about 90 weight percent based on total weight of the absorbent assembly. The absorbent assembly 44 suitably has a density within the range of about 0.10 to about 0.35 grams per cubic centimeter. The absorbent assembly 44 may or may not be wrapped or encompassed by a suitable tissue wrap that maintains the integrity and/or shape of absorbent assembly.

The absorbent chassis 32 can also incorporate other materials that are designed primarily to receive, temporarily store, and/or transport liquid along the mutually facing surface with absorbent assembly 44, thereby maximizing the absorbent capacity of absorbent assembly. One suitable material is referred to as a surge layer (not shown) and comprises a material having a basis weight of about 50 grams per square meter, and comprising a through-air-bonded-carded web of a homogenous blend of 60 percent 3 denier bicomponent fiber comprising a polyester core/polyethylene sheath, commercially available from BASF Corporation, and 40 percent 6 denier polyester fiber, commercially available from Hoechst Celanese.

Figure 7A:
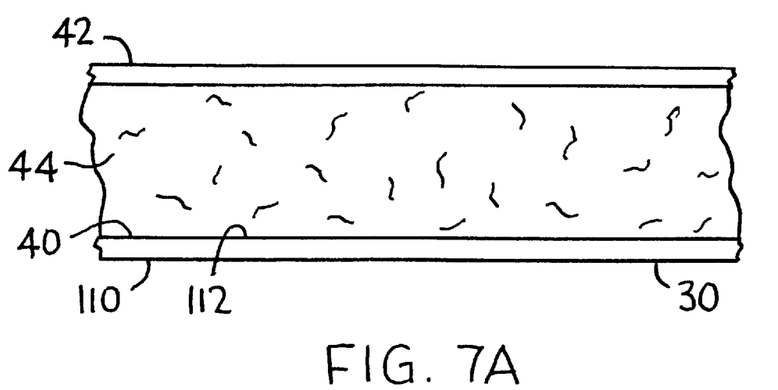
FIGS. 7A, 7B and 7C illustrate various partial section views of absorbent articles according to the present invention.
Figure 7B:
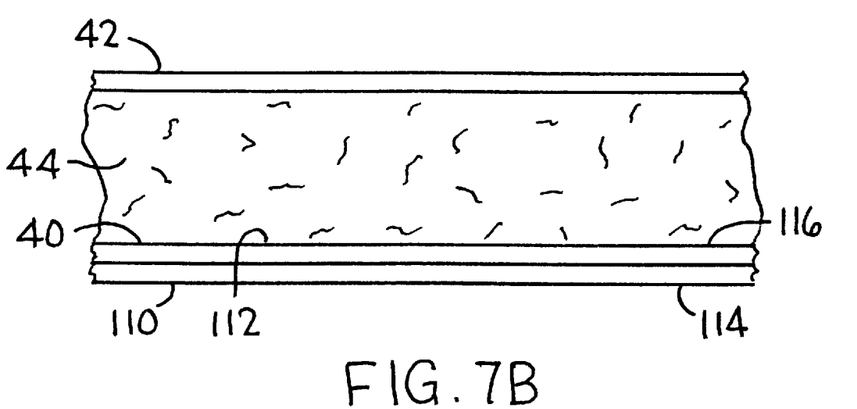
Figure 7C:
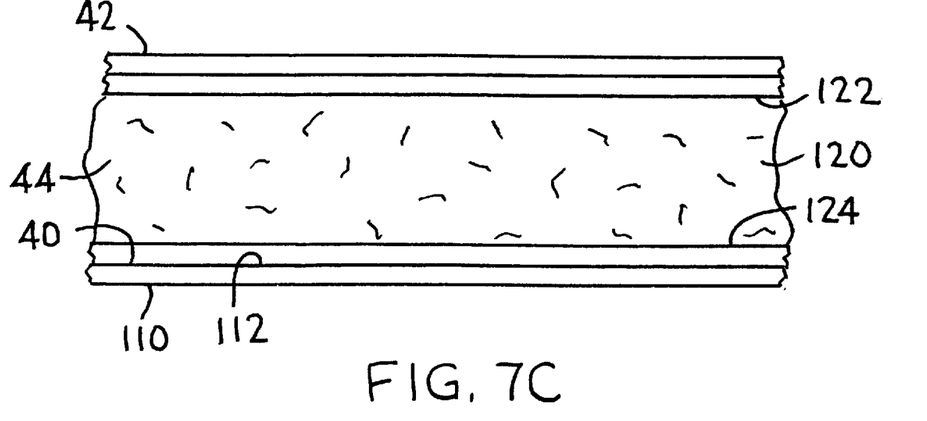

Various placements of the permanent and active graphics may be better understood with reference to the partial section views of absorbent articles that are shown in FIGS. 7A, 7B and 7C. The various layers of the illustrated embodiments can be secured together using adhesives, thermal bonds, mechanical bonds, or other means known to those skilled in the art.

FIG. 7A illustrates a partial section view of an absorbent article having an absorbent assembly 44 sandwiched between an outer cover 40 and a bodyside liner 42. The illustrated outer cover 40 consists of a single layer having an exterior surface 110 and an opposite interior surface 112. The permanent and active graphics can be disposed on the outer cover 40, which includes on either surface 110 or 112 of the outer cover, on the surface of the absorbent assembly 44 that faces the outer cover, or between the absorbent assembly and the outer cover. The outer cover 40 is desirably formed of a material that is liquid impermeable. In such embodiments and where the active graphics are triggered by contact with urine, it is desirable for the active graphics to be disposed on the interior surface 112 of the outer cover 40, on the surface of the absorbent assembly 44 that faces the outer cover, or between the absorbent assembly and the outer cover. The permanent and active graphics need not be located in the same position or on the same substrate.

FIG. 7B illustrates a partial section view of another absorbent article having an absorbent assembly 44 sandwiched between an outer cover 40 and a bodyside liner 42. The illustrated outer cover 40 consists of a two-layer composite comprising an outer layer 114 and an inner layer 116. The outer cover 40 has an exterior surface 110 and an opposite interior surface 112. The permanent and active graphics can be disposed on the outer cover 40, which includes, in particular, on the exterior surface 110, on the interior surface 112, between the outer and inner layers 114 and 116, on either or both facing surfaces of the outer and inner layers 114 and 116, on the surface of the absorbent assembly 44 that faces the outer cover, or between the absorbent assembly and the outer cover.

FIG. 7C illustrates a partial section view of a further absorbent article having an absorbent assembly 44 sandwiched between an outer cover 40 and a bodyside liner 42. The illustrated absorbent assembly includes a liquid storage layer 120 sandwiched between absorbent assembly substrates 122 and 124. The substrates 122 and 124 can comprise tissue wrap sheets, liquid distribution or liquid handling layers, or the like. The illustrated outer cover 40 consists of a single layer having an exterior surface 110 and an opposite interior surface 112, but can alternatively comprise a multiple-layer composite. The permanent and active graphics can be disposed on the outer cover 40, which includes specific locations such as on the exterior surface 110, on the interior surface 112, on either surface of the substrate 124 that is placed with or placed near the outer cover, between the substrate 124 and the outer cover, on the surface of the liquid storage layer 120 that faces the outer cover, or between the liquid storage layer and the substrate 124. Various other locations for the permanent and active graphics can be suitable where different configurations of the absorbent assembly 44 and outer cover 40 are employed, including but not limited to within a layer of the absorbent assembly or outer cover.

As noted previously, the illustrated training pant 20 has a side panel 34 disposed on each side of the absorbent chassis 32. In the illustrated embodiment, the pair of transversely opposed side panels 34 are permanently bonded to the absorbent chassis 32 and permanently bonded to one another, using attachment means known to those skilled in the art such as adhesive, thermal or ultrasonic bonding.

The side panels 34 desirably comprise an elastic material capable of stretching in a direction parallel to the transverse axis 49 of the training pant 20. Suitable elastic materials, as well as one described process of incorporating elastic side panels into a training pant, are described in the following U.S. Pat. Nos.: 4,940,464 issued Jul. 10, 1990 to Van Gompel et al.; 5,224,405 issued Jul. 6, 1993 to Pohjola; 5,104,116 issued Apr. 14, 1992 to Pohjola; and 5,046,272 issued Sep. 10,1991 to Vogt et al.; all of which are incorporated herein by reference. In particular embodiments, the elastic material comprises a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Mormon; and European Patent Application No. EP 0 217 032 published on Apr. 8, 1987 in the names of Taylor et al.; all of which are incorporated herein by reference. Alternatively, the side panel material can comprise other woven or nonwoven materials, such as those described above as being suitable for the outer cover 40 or bodyside liner 42.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. An absorbent article comprising:
    an outer cover having an interior surface and an opposite exterior surface;
    an absorbent assembly disposed on the interior surface;
    a permanent character graphic disposed on the outer cover;
    an active object graphic disposed on the outer cover;
    wherein the permanent character graphic is interactively interrelated with the active object graphic, and the permanent object graphic is related in subject matter to the active object graphic.

2. An absorbent article comprising:
    an outer cover having an interior surface and an opposite exterior surface;
    an absorbent assembly disposed on the interior surface;
    a permanent character graphic disposed on the outer cover;
    a permanent object graphic disposed on the outer cover;
    an active object graphic disposed on the outer cover;
    wherein the permanent character graphic is interactively interrelated with the permanent object graphic and the active object graphic.

3. An absorbent article comprising:
    an outer cover having an interior surface and an opposite exterior surface;
    an absorbent assembly disposed on the interior surface;
    a permanent character graphic disposed on the outer cover;
    an active object graphic disposed on the outer cover, further comprising a permanent object graphic, wherein the permanent character graphic, the permanent object graphic and the active object graphic are related by a common story line.

4. The absorbent article of claim 1, 2 or 3, wherein the permanent character graphic is illustrated to be involved in an activity utilizing the permanent object graphic, and the active object graphic is the subject of the activity.

5. The absorbent article of claim 1 or 2, wherein the active object graphic comprises an ink that is soluble in urine and the active object graphic is in liquid communication with the absorbent assembly.

6. The absorbent article of claim 1 or 2, wherein the active object graphic comprises an ink that changes color when exposed to urine and the active object graphic is in liquid communication with the absorbent assembly.

7. The absorbent article of claim 1 or 2, wherein the active object graphic comprises an appearing graphic that becomes significantly more visible when exposed to urine and the active object graphic is in liquid communication with the absorbent assembly.

8. The absorbent article of claim 1 or 2, wherein the active object graphic comprises an appearing graphic that becomes significantly more visible when exposed to an environment during use and prior to contact with urine.

9. The absorbent article of claim 1 or 2, wherein the active object graphic is disposed on the interior surface of the outer cover.

10. The absorbent article of claim 1 or 2, wherein the outer cover comprises a liquid permeable outer layer and a liquid impermeable inner layer, the active object graphic is disposed on one surface of the inner layer that forms the interior surface of the outer cover, and the permanent character graphic is disposed on an opposite surface of the inner layer.

11. The absorbent article of claim 1 or 2, wherein the active object graphic is disposed on a surface of the absorbent assembly that faces the outer cover.

12. The absorbent article of claim 1 or 2, wherein the outer cover is adhesively attached to the absorbent assembly in a windowpane pattern, and a region of the outer cover containing the active object graphic is unadhered to the absorbent assembly.

13. The absorbent article of claim 1 or 2, wherein the active object graphic comprises lines having a line width of from about 1 to about 2 millimeters.

14. The absorbent article of claim 1 or 2, wherein the absorbent article defines a longitudinal centerline and a transverse centerline, and the absorbent article comprises a plurality of active object graphics that are located in a distinct active graphic region having a length dimension measured parallel to the longitudinal centerline of about 10 centimeters and a width dimension measured parallel to the transverse centerline of about 6 centimeters.

15. The absorbent article of claim 14, wherein the active graphic region is spaced from a first longitudinal end edge of the absorbent article by approximately 13 to 16 centimeters.

16. The absorbent article of claim 1 or 2, wherein the absorbent article defines a longitudinal centerline, a transverse centerline, opposite first and second longitudinal end edges, first and second waist regions abutting the respective first and second longitudinal end edges, and a crotch region disposed between and interconnecting the first and second waist regions, the permanent character graphic being disposed in the first waist region and the active object graphic being disposed in the crotch region.

17. The absorbent article of claim 16, wherein the active object graphic is longitudinally disposed between the permanent character graphic and the transverse centerline.

18. The absorbent article of claim 1 or 2, wherein the absorbent article comprises from 4 to 8 active object graphics that have a size of at least about 1.5 by 1.5 centimeter and less than about 3 by 3 centimeters.

19. The absorbent article of claim 18, wherein the permanent character graphic has a size that is at least twice as large as the size of the active object graphics.

20. A disposable absorbent training pant defining a longitudinal centerline, a transverse centerline, opposite first and second longitudinal end edges, first and second waist regions abutting the respective first and second longitudinal end edges, and a crotch region disposed between and interconnecting the first and second waist regions, the absorbent article comprising:
    a liquid impermeable outer cover having an interior surface and an opposite exterior surface;
    an absorbent assembly disposed on the interior surface of the outer cover;
    a liquid permeable liner disposed on the absorbent assembly sandwiching the absorbent assembly between the outer cover and the liner;

a permanent character graphic disposed on the outer cover in the first waist region;

a permanent object graphic disposed on the outer cover;

a plurality of active object graphics disposed on the outer cover in the crotch region between the permanent character graphic and the transverse centerline, the active object graphics being in liquid communication with the absorbent assembly;

wherein the permanent character graphic, the permanent object graphic and the active object graphics are related by a common story line in which the permanent character graphic is involved in an activity utilizing the permanent object graphic, and the active object graphics are the subject of the activity.

21. The training pant of claim 20, wherein the active object graphics comprise an ink that is soluble in urine.

22. The training pant of claim 20, wherein the active object graphics comprise an ink that changes color when exposed to urine.

23. The training pant of claim 20, wherein the outer cover comprises a liquid permeable outer layer and a liquid impermeable inner layer, the active object graphics are disposed on one surface of the inner layer and the permanent character graphic is disposed on an opposite surface of the inner layer.

24. The training pant of claim 20, wherein the outer cover is adhesively attached to the absorbent assembly in a windowpane pattern, and a region of the outer cover containing the active object graphic is unadhered to the absorbent assembly.

* * * * *

UNITED STATES PATENT AND TRADEMARK OFFICE
CERTIFICATE OF CORRECTION

PATENT NO. : 6,297,424 B1
DATED : October 2, 2001
INVENTOR(S) : Christopher Peter Olson, Kathleen Irene Ratliff and Shirlee Ann Weber It is certified that error appears in the above-identified patent and that said Letters Patent is hereby corrected as shown below:

<u>Column 17,</u>
Line 16, insert -- a permanent object graphic disposed on the outer cover; -- as a new line under "a permanent character graphic disposed on the outer cover".

Signed and Sealed this

Fifteenth Day of October, 2002

*Attest:*

*Attesting Officer*

JAMES E. ROGAN
*Director of the United States Patent and Trademark Office*